United States Patent
Zhang (10) Patent No.: US 11,579,226 B2
(45) Date of Patent: Feb. 14, 2023

(54) SYSTEM AND METHOD FOR TIME OF FLIGHT IMAGING WITH A TIGHT SEQUENCE DIAGRAM PATTERN

(71) Applicant: Siemens Healthcare GmbH, Erlangen (DE)

(72) Inventor: Qiong Zhang, Shenzhen (CN)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 17/476,699

(22) Filed: Sep. 16, 2021

(65) Prior Publication Data

US 2022/0082646 A1    Mar. 17, 2022

(30) Foreign Application Priority Data

Sep. 16, 2020 (CN) .......................... 202010973319.8

(51) Int. Cl.
| | | |
|---|---|---|
| *G01R 33/483* | (2006.01) | |
| *A61B 5/055* | (2006.01) | |
| *G06T 7/00* | (2017.01) | |

(52) U.S. Cl.
CPC .......... *G01R 33/4835* (2013.01); *A61B 5/055* (2013.01); *G01R 33/4838* (2013.01); *G06T 7/0012* (2013.01); *G06T 2207/10088* (2013.01)

(58) Field of Classification Search
CPC ............ G01R 33/4835; G01R 33/4838; G01R 33/5635; A61B 5/055; G06T 7/0012; G06T 2207/10088
See application file for complete search history.

(56) References Cited

U.S. PATENT DOCUMENTS

| 6,188,922 B1 | 2/2001 | Mistretta et al. |
| 2003/0166999 A1 | 9/2003 | Liu et al. |
| 2021/0181285 A1* | 6/2021 | Stemmer ............ G01R 33/5617 |

FOREIGN PATENT DOCUMENTS

| CN | 105608702 A | 5/2016 |
| KR | 101373563 B1 | 3/2014 |
| KR | 101507762 B1 | 4/2015 |
| KR | 2015045659 A | 4/2015 |
| KR | 101634045 B1 | 6/2016 |
| KR | 101848126 B1 | 4/2018 |
| KR | 101996476 B1 | 7/2019 |

* cited by examiner

*Primary Examiner* — Susan S Lee
(74) *Attorney, Agent, or Firm* — Banner & Witcoff Ltd.

(57) ABSTRACT

A Time-of-flight (TOF) MRI scanning method may include: a TOF MRI scan including a first slice selection gradient applied in the Z direction at the same time as an RF pulse being applied to an imaging target; after applying the RF pulse and first slice selection gradient has ended, applying a slice selection encoding gradient and a phase encoding gradient in the Z direction and Y direction respectively; when application of the slice selection encoding gradient and phase encoding gradient ends, applying a readout gradient in the X direction; when application of the readout gradient ends, applying a tracking saturation pulse to the imaging target, and simultaneously applying a second slice selection gradient in the Z direction; when application of the tracking saturation pulse ends, applying a spoiler gradient in the X, Y and/or Z directions of the magnetic field. The method advantageously reduces the TOF MRI scanning time.

14 Claims, 7 Drawing Sheets

FIG. 1

(related art)

SYSTEM AND METHOD FOR TIME OF FLIGHT IMAGING WITH A TIGHT SEQUENCE DIAGRAM PATTERN

CROSS REFERENCE TO RELATED APPLICATIONS

This patent application claims priority to Chinese Patent Application No. 202010973319.8, filed Sep. 16, 2020, which is incorporated herein by reference in its entirety.

BACKGROUND

Technical Field

The present disclosure relates to the technical field of MRI (magnetic resonance imaging), in particular to a TOF (time of flight) MRI scanning method and apparatus, and an MRI system.

Related Art

In MRI, an RF (radio frequency) pulse of a specific frequency is applied to a human body in a static magnetic field, such that hydrogen protons in the human body are excited and experience the phenomenon of MR (magnetic resonance). When the pulse is stopped, the protons give rise to MR signals in the course of relaxation. The MR signals are received and undergo processing such as spatial encoding and image reconstruction to produce an MR image.

In the course of imaging, after RF excitation, slice selection is first accomplished via a gradient in the Z direction, i.e. a slice to be imaged is selected; the magnetic field in the Y direction is then switched on, such that the speeds of precession of magnetic moments at different Y positions will also be different, and the Y gradient is then switched off, such that the speeds of the magnetic moments at the various positions return to being the same, but due to the different phase shifts at different Y positions caused by the different speeds of precession previously, this process is called phase encoding; and a gradient in the X direction is then switched on, such that the speeds of magnetic moments are different at different X positions, this process being called frequency encoding. Thus, phase encoding and frequency encoding enable each position of a 2D image to be determined, and signals collected by a receiving coil are k space signals, which undergo a Fourier transform to obtain an image; a new slice selection is then performed by means of the gradient in the Z direction, and the above process is then repeated to obtain a 3D MRI image.

In MRI, after stationary tissue has experienced slice selection gradients (i.e. Z direction gradients) of the same size but in opposite directions, the phase accumulation obtained is zero; but the phase accumulation is not zero for moving tissue that moves in the direction of the readout gradient field (i.e. the X direction) such as flowing blood and cerebrospinal fluid, etc.; when the next phase encoding gradient (i.e. Y direction gradient) is applied, moving tissue that already has a phase will be incorrectly encoded, and appear at another position, thus becoming a flow artefact.

FC (Flow Compensation), also called GMN (Gradient Moment Nulling), is a technique for reducing or eliminating flow artefacts by using a specially designed gradient field. There are many types of gradient combination mode in the FC technique. Alternating between forward and reverse gradient fields of different areas multiple times ultimately enables all of the phase shifts of fluids of various speeds to approach zero, thereby eliminating motion artefacts. In general, FC compensates for the effects of uniform-speed flow by eliminating first-order gradient moments.

TOF (Time of Flight) imaging is established on gradient echo scanning with flow compensation. This type of imaging technique mainly relies on a flow enhancement effect to differentiate between moving and fixed protons, in order to form a magnetic resonance blood vessel contrast image.

Figure 1:
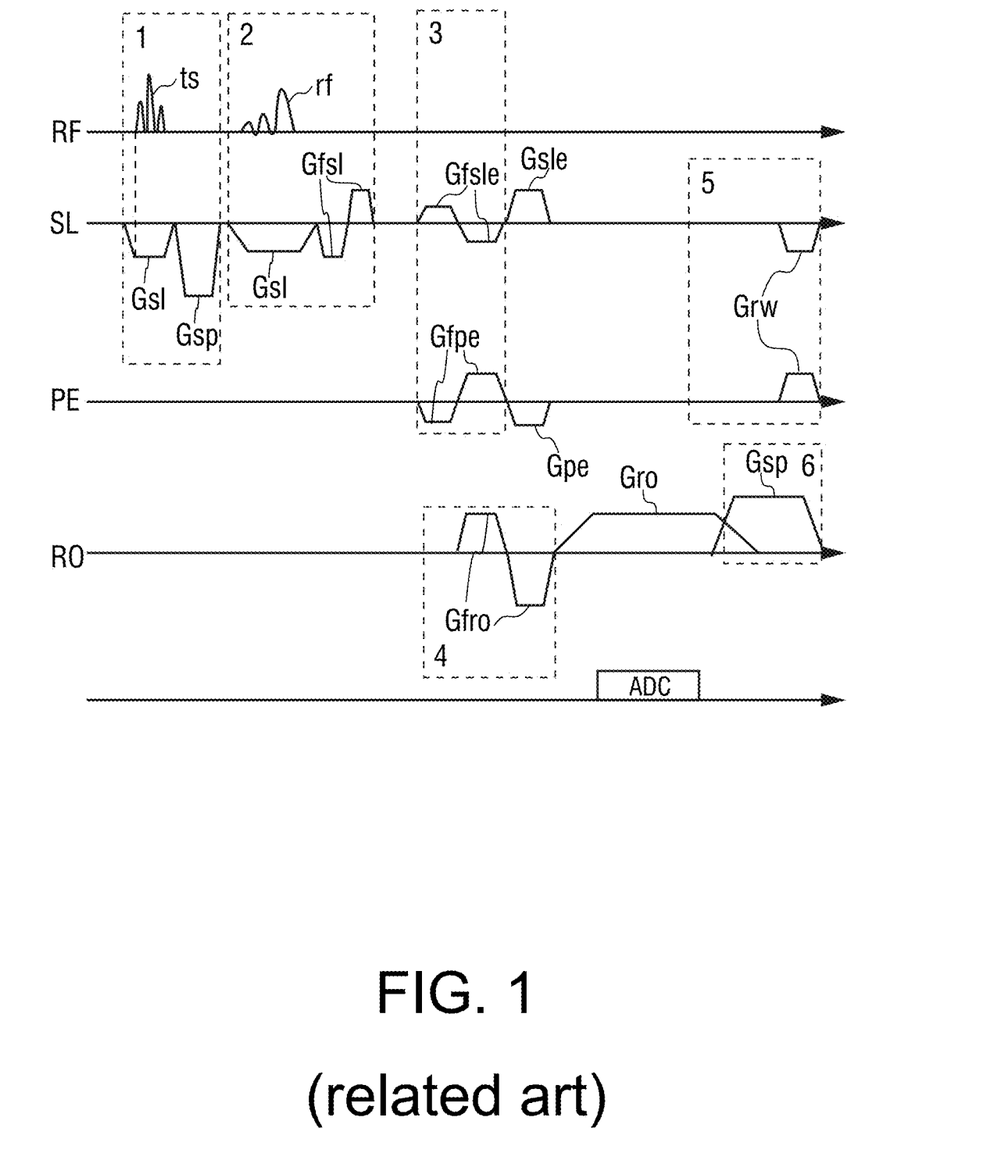
FIG. 1 is a schematic diagram of a conventional TOF sequence.

A TOF sequence in current use is as shown in FIG. 1, being composed of four main parts: RF: radio frequency sequence, SL: slice selection sequence, PE: phase encoding sequence and RO: readout sequence. In order to describe the characteristics of the TOF sequence clearly, it is divided into the following 6 modules:

module 1: before radio frequency (rf) excitation, a tracking saturation (ts) pulse is applied, so as to suppress a vein signal; at the same time, a spoiler gradient Gsp is applied in the magnetic field Z direction, for the purpose of eliminating a surplus transverse magnetization signal;

module 2: at the same time as radio frequency (rf) excitation is performed, a slice selection (SL) gradient Gsl is applied in the magnetic field Z direction, and when application of the slice selection gradient Gsl has ended, a flow compensation gradient Gfsl is applied;

module 3: after radio frequency (rf) excitation, a slice selection encoding gradient Gsle is applied in the magnetic field Z direction, with a phase encoding (PE) gradient Gpe being applied in the magnetic field Y direction at the same time; moreover, flow compensation gradients Gfsle and Gfpe are applied before application of the slice selection encoding gradient Gsle and phase encoding gradient Gpe respectively, wherein the two flow compensation gradients Gfsle and Gfpe are optional, e.g.: in 3T MRI, the two flow compensation gradients are not applied;

module 4: when the application of the slice selection encoding gradient Gsle and phase encoding gradient Gpe has ended, a readout (RO) gradient Gro is applied in the magnetic field X direction, and a flow compensation gradient Gfro is applied before application of the readout gradient Gro;

module 5: at the end of the TOF sequence, a refocusing gradient Grw is applied in the magnetic field Z direction and Y direction, to cancel out the previous gradients;

module 6: when the application of the readout gradient in the magnetic field X direction has ended, a spoiler gradient Gsp is applied, for the purpose of eliminating a surplus transverse magnetization signal.

As can be seen, the existing TOF sequence includes a considerable number of gradients: the flow compensation gradients, refocusing gradient and spoiler gradients, and consequently the TR (Time of Repetition) is long.

BRIEF DESCRIPTION OF THE DRAWINGS/FIGURES

The accompanying drawings, which are incorporated herein and form a part of the specification, illustrate the embodiments of the present disclosure and, together with the description, further serve to explain the principles of the embodiments and to enable a person skilled in the pertinent art to make and use the embodiments.

The exemplary embodiments of the present disclosure will be described with reference to the accompanying drawings. Elements, features and components that are identical, functionally identical and have the same effect are—insofar as is not stated otherwise—respectively provided with the same reference character.

DETAILED DESCRIPTION

In the following description, numerous specific details are set forth in order to provide a thorough understanding of the embodiments of the present disclosure. However, it will be apparent to those skilled in the art that the embodiments, including structures, systems, and methods, may be practiced without these specific details. The description and representation herein are the common means used by those experienced or skilled in the art to most effectively convey the substance of their work to others skilled in the art. In other instances, well-known methods, procedures, components, and circuitry have not been described in detail to avoid unnecessarily obscuring embodiments of the disclosure. The connections shown in the figures between functional units or other elements can also be implemented as indirect connections, wherein a connection can be wireless or wired. Functional units can be implemented as hardware, software or a combination of hardware and software.

An object of the present disclosure is to provide a TOF MRI scanning method and apparatus, and also propose an MRI system, with the aim of reducing the TOF MRI scanning time.

In an exemplary embodiment, a Time-of-flight (TOF) MRI scanning method, includes: a TOF MRI scan beginning, with a first slice selection gradient being applied in the Z direction of a magnetic field at the same time as an RF pulse is applied to an imaging target;
after the application of the RF pulse and first slice selection gradient has ended, applying a slice selection encoding gradient and a phase encoding gradient in the Z direction and Y direction of the magnetic field respectively;
when the application of the slice selection encoding gradient and phase encoding gradient ends, beginning the application of a readout gradient in the X direction of the magnetic field;
when the application of the readout gradient ends, beginning the application of a tracking saturation pulse to the imaging target, and simultaneously beginning the application of a second slice selection gradient in the Z direction of the magnetic field;
when the application of the tracking saturation pulse ends, beginning the application of a spoiler gradient in one of the three directions X, Y and Z of the magnetic field or any combination thereof.

In an exemplary embodiment, when the application of the tracking saturation pulse ends, the method further comprises: beginning the application of a refocusing gradient in one of the two directions Y and Z of the magnetic field or a combination thereof.

In an exemplary embodiment, after the application of the first slice selection gradient in the Z direction of the magnetic field, the method further comprises: when the application of the first slice selection gradient ends, beginning the application of a first flow compensation gradient in the Z direction of the magnetic field.

In an exemplary embodiment, after the application of the RF pulse and first slice selection gradient has ended, and before the application of the slice selection encoding gradient and phase encoding gradient in the Z direction and Y direction of the magnetic field respectively, the method further comprises: applying a second flow compensation gradient and a third flow compensation gradient of the same length in the Z direction and Y direction of the magnetic field simultaneously.

In an exemplary embodiment, the application of the slice selection encoding gradient and phase encoding gradient in the Z direction and Y direction of the magnetic field respectively comprises: beginning the application of the slice selection encoding gradient and phase encoding gradient in the Z direction and Y direction of the magnetic field respectively when the application of the second flow compensation gradient and third flow compensation gradient ends.

In an exemplary embodiment, after beginning the application of the first flow compensation gradient in the Z direction of the magnetic field and before beginning the application of the readout gradient in the X direction of the magnetic field, the method further comprises: applying a fourth flow compensation gradient in the X direction of the magnetic field;

In an exemplary embodiment, the step of beginning the application of the readout gradient in the X direction of the magnetic field comprises: beginning the application of the readout gradient in the X direction of the magnetic field when the application of flow compensation in the X direction of the magnetic field ends.

In an exemplary embodiment, a Time-of-flight (TOF) MRI scanning apparatus, includes a first scanning controller and a second scanning controller.

In an exemplary embodiment, the first scanning controller is configured to: apply a first slice selection gradient in the Z direction of a magnetic field at the same time as applying an RF pulse to an imaging target when a TOF MRI scan begins; apply a slice selection encoding gradient and a phase encoding gradient in the Z direction and Y direction of the magnetic field respectively, after the application of the RF pulse and first slice selection gradient has ended; begin the application of a readout gradient in the X direction of the magnetic field, when the application of the slice selection encoding gradient and phase encoding gradient ends; begin the application of a tracking saturation pulse to the imaging target, and simultaneously begin the application of a second slice selection gradient in the Z direction of the magnetic field, when the application of the readout gradient ends.

In an exemplary embodiment, the second scanning controller is configured to begin the application of a spoiler gradient in one of the three directions X, Y and Z of the magnetic field or any combination thereof, when the application of the tracking saturation pulse ends.

In an exemplary embodiment, when the application of the tracking saturation pulse ends, the second scanning controller is further configured to: begin the application of a refocusing gradient in one of the two directions Y and Z of the magnetic field or a combination thereof.

In an exemplary embodiment, after applying the first slice selection gradient in the Z direction of the magnetic field, the first scanning controller is further configured to: when the application of the first slice selection gradient ends, beginning the application of a first flow compensation gradient in the Z direction of the magnetic field.

In an exemplary embodiment, after the application of the RF pulse and first slice selection gradient has ended, and before the application of the slice selection encoding gradient and phase encoding gradient in the Z direction and Y direction of the magnetic field respectively, the first scanning controller is further configured to: apply a second flow compensation gradient and a third flow compensation gradient of the same length in the Z direction and Y direction of the magnetic field simultaneously.

In an exemplary embodiment, the application of the slice selection encoding gradient and phase encoding gradient in the Z direction and Y direction of the magnetic field respectively by the first scanning controller comprises: beginning the application of the slice selection encoding gradient and phase encoding gradient in the Z direction and Y direction of the magnetic field respectively when the application of the second flow compensation gradient and third flow compensation gradient ends.

In an exemplary embodiment, after beginning the application of the first flow compensation gradient in the Z direction of the magnetic field and before beginning the application of the readout gradient in the X direction of the magnetic field, the first scanning controller is further configured to: apply a fourth flow compensation gradient in the X direction of the magnetic field.

The step of beginning the application of the readout gradient in the X direction of the magnetic field by the first scanning controller may include: beginning the application of the readout gradient in the X direction of the magnetic field when the application of flow compensation in the X direction of the magnetic field ends.

An aspect of the present disclosure is directed to an MRI system that includes any one of the TOF MRI scanning apparatuses described above. In one or more of the embodiments of the present disclosure, the tracking saturation pulse is applied after the readout gradient, and the application of the spoiler gradient is begun in one of the three directions X, Y and Z of the magnetic field or any combination thereof when the application of the tracking saturation pulse ends, and hence the spoiler gradient only needs to be applied once, so the repetition time (TR) of the TOF sequence is reduced and the TOF MRI scanning time is reduced; moreover, due to the reduction in TR, the signal strength of background tissue in the MRI image finally obtained is reduced, and therefore the contrast between foreground (e.g. arteries) and background tissue is enhanced.

Figure 2:
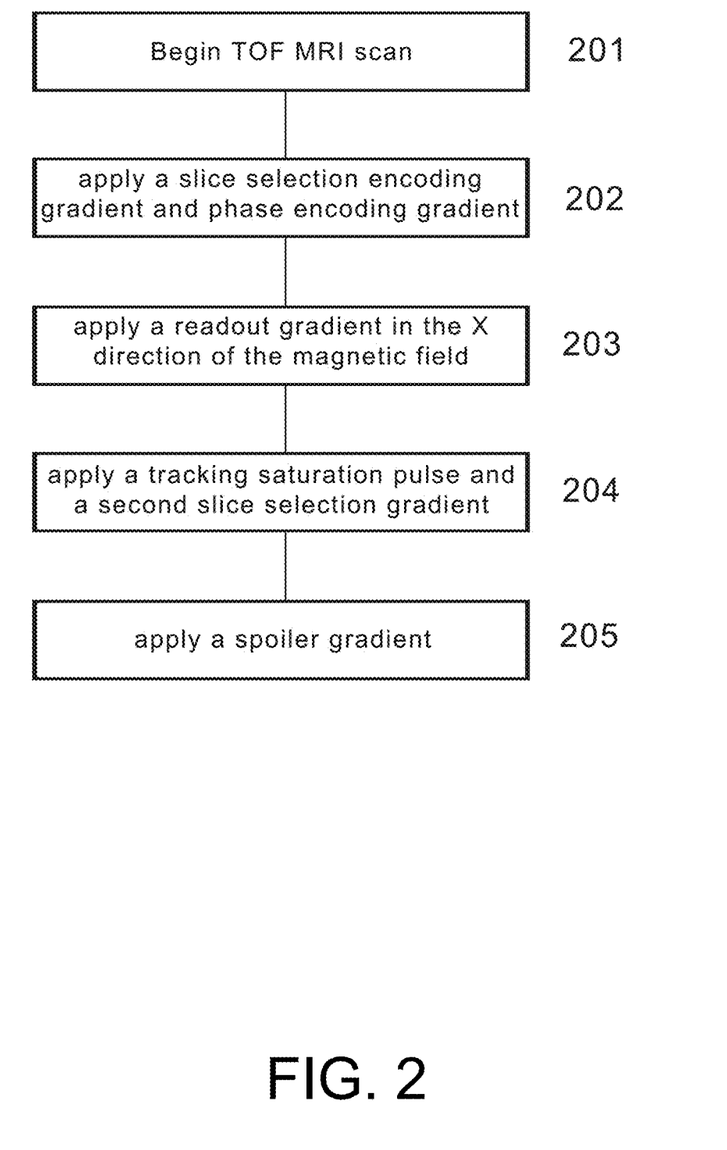
FIG. 2 is a flow chart of a TOF MRI scanning method according to an exemplary embodiment of the present disclosure.

FIG. 2 is a flow chart of a TOF MRI scanning method provided in an embodiment of the present disclosure, having the following specific steps:

Step 201: a TOF MRI scan begins, with a first slice selection gradient being applied in the Z direction of the magnetic field at the same time as an RF pulse is applied to the imaging target.

Step 202: after application of the RF pulse and first slice selection gradient has ended, a slice selection encoding gradient and a phase encoding gradient are applied in the Z direction and Y direction of the magnetic field respectively.

Step 203: when the application of the slice selection encoding gradient and phase encoding gradient ends, the application of a readout gradient in the X direction of the magnetic field is begun.

Step 204: when the application of the readout gradient ends, the application of a tracking saturation pulse to the imaging target is begun, and the application of a second slice selection gradient in the Z direction of the magnetic field is begun simultaneously.

Step 205: when the application of the tracking saturation pulse ends, the application of a spoiler gradient is begun in one of the three directions X, Y and Z of the magnetic field or any combination thereof.

That is to say, a spoiler gradient is applied in one of the three directions X, Y and Z of the magnetic field, or spoiler gradients are applied in any two of the three directions X, Y and Z of the magnetic field, or spoiler gradients are applied in the three directions X, Y and Z of the magnetic field simultaneously. The effect of the spoiler gradient is to eliminate a surplus transverse magnetization signal. When spoiler gradients are applied in two or more directions, all of the applied spoiler gradients have the same length.

The above steps 201-205 are repeated, and k-space signals collected by a receiving coil are subjected to a Fourier transform to obtain a 3D MRI image of the imaging target.

In the above embodiment, the tracking saturation pulse is applied after the readout gradient, and the application of the spoiler gradient is begun in one of the three directions X, Y and Z of the magnetic field or any combination thereof when the application of the tracking saturation pulse ends, and hence the spoiler gradient only needs to be applied once, so the repetition time (TR) of the TOF sequence is reduced and the TOF MRI scanning time is reduced; moreover, due to the reduction in TR, the signal strength of background tissue in the MRI image finally obtained is reduced, and therefore the contrast between foreground (e.g. arteries) and background tissue is enhanced.

In an optional embodiment, in step 205, when the application of the tracking saturation pulse ends, the method further comprises: beginning the application of a refocusing gradient in one of the two directions Y and Z of the magnetic field or a combination thereof.

The refocusing gradient and each spoiler gradient are all of the same length.

In the above embodiment, the application of the refocusing gradient is begun in one of the two directions Y and Z of the magnetic field or a combination thereof when the application of the tracking saturation pulse ends, thus the spoiler gradient and refocusing gradient are applied simultaneously, so compared with the existing TOF sequence, the TR is still reduced, and the TOF MRI scanning time is still reduced.

In an optional embodiment, in step 201, after the application of the first slice selection gradient in the Z direction of the magnetic field, the method further comprises: when the application of the first slice selection gradient ends, beginning the application of a first flow compensation gradient in the Z direction of the magnetic field.

In an optional embodiment, in step 202, after the application of the RF pulse and first slice selection gradient has ended, and before the application of the slice selection encoding gradient and phase encoding gradient in the Z direction and Y direction of the magnetic field respectively, the method further comprises: applying a second flow compensation gradient and a third flow compensation gradient of the same length in the Z direction and Y direction of the magnetic field simultaneously;

and the application of the slice selection encoding gradient and phase encoding gradient in the Z direction and Y direction of the magnetic field respectively comprises: beginning the application of the slice selection encoding gradient and phase encoding gradient in the Z direction and Y direction of the magnetic field respectively when the application of the second flow compensation gradient and third flow compensation gradient ends.

In an optional embodiment, after "beginning the application of a first flow compensation gradient in the Z direction of the magnetic field" in step 201 and before "the application of a readout gradient in the X direction of the magnetic field is begun" in step 203, the method further comprises: applying a fourth flow compensation gradient in the X direction of the magnetic field;

and the step of beginning the application of the readout gradient in the X direction of the magnetic field comprises: beginning the application of the readout gradient in the X direction of the magnetic field when the application of flow compensation in the X direction of the magnetic field ends.

The above embodiment achieves flow compensation of the slice selection gradient, slice selection encoding gradient, phase encoding gradient and readout gradient, thereby improving the quality of the magnetic resonance image finally obtained.

FIGS. 3-7 are exemplary diagrams of five TOF sequences provided in embodiments of the present disclosure, wherein the labels have the following meanings:
1. RF: radio frequency sequence, rf: radio frequency pulse, ts: tracking saturation pulse;
2. SL: slice selection sequence, Gsl: slice selection gradient, Gfsl: flow compensation gradient for slice selection gradient, Gsle: slice selection encoding gradient, Gfsle: flow compensation gradient for slice selection encoding gradient;
3. PE: phase encoding sequence, Gpe: phase encoding gradient, Gfpe: flow compensation gradient for phase encoding gradient;
4. RO: readout sequence, Gro: readout gradient, Gfro: flow compensation gradient for readout gradient;
5. Gsp: spoiler gradient; and
6. Grw: refocusing gradient.

In the TOF sequences shown in FIGS. 3-6, spoiler gradients Gsp are applied but not refocusing gradients Grw.

Figure 3:
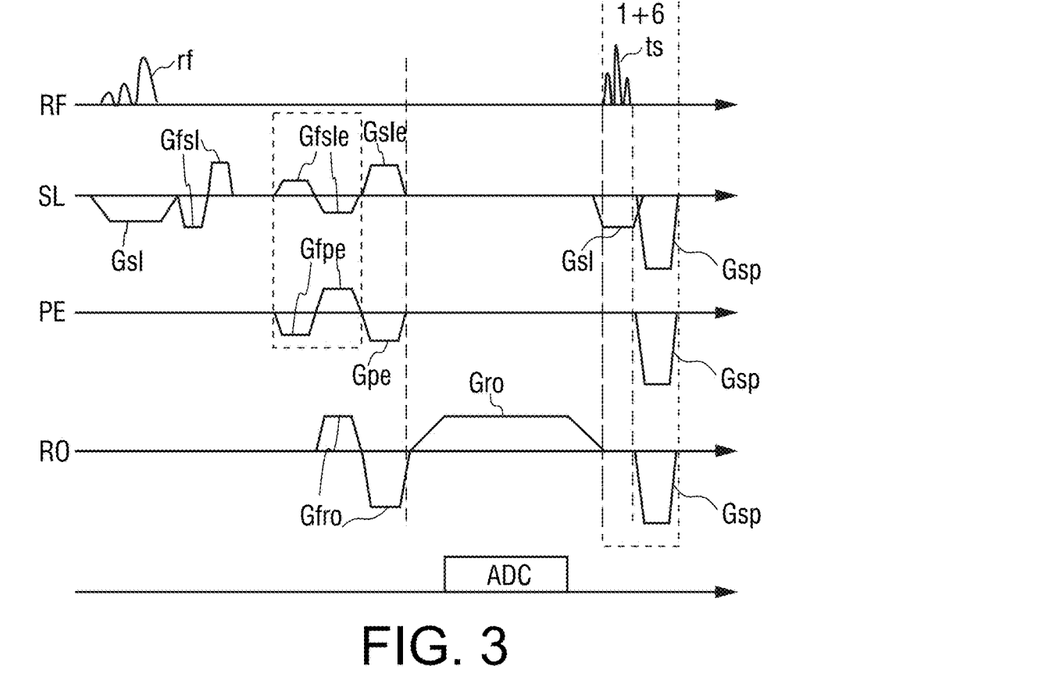
FIG. 3 is a schematic diagram of a TOF sequence according to an exemplary embodiment of the present disclosure.
Figure 4:
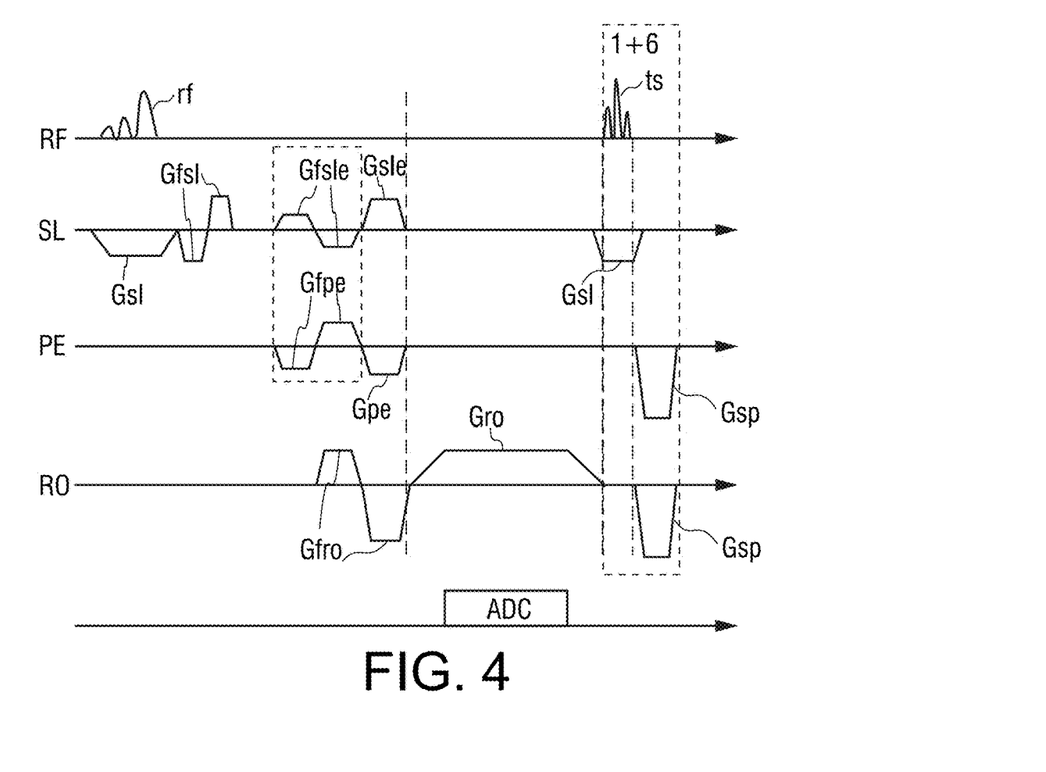
FIG. 4 is a schematic diagram of a TOF according to an exemplary embodiment of the present disclosure.
Figure 5:
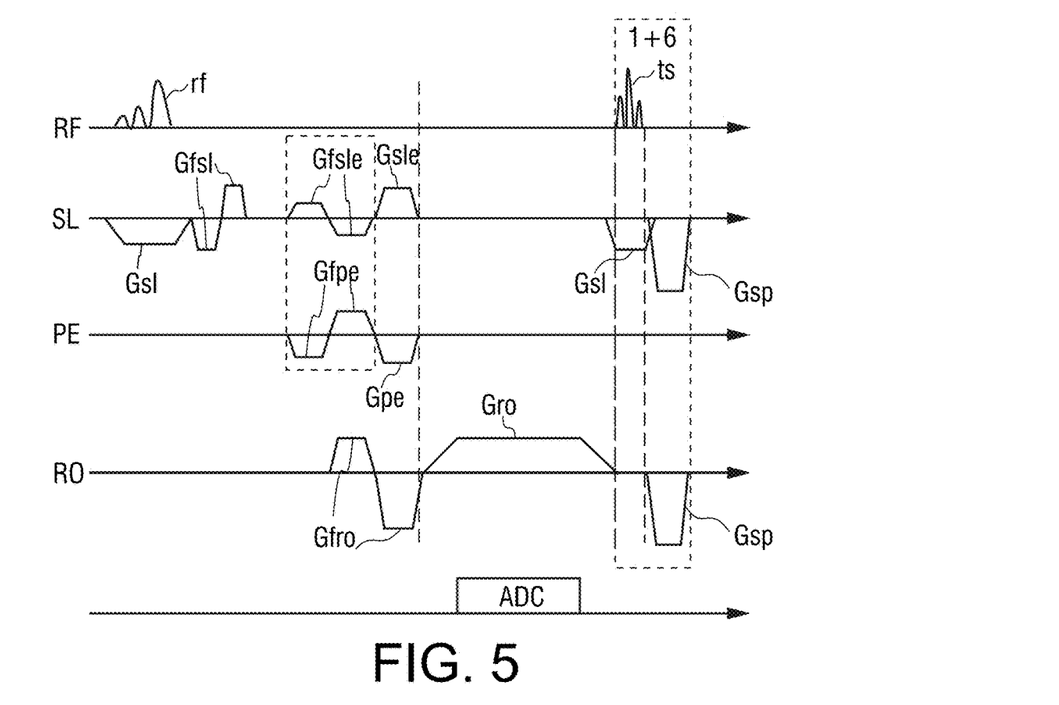
FIG. 5 is a schematic diagram of a TOF sequence according to an exemplary embodiment of the present disclosure.
Figure 6:
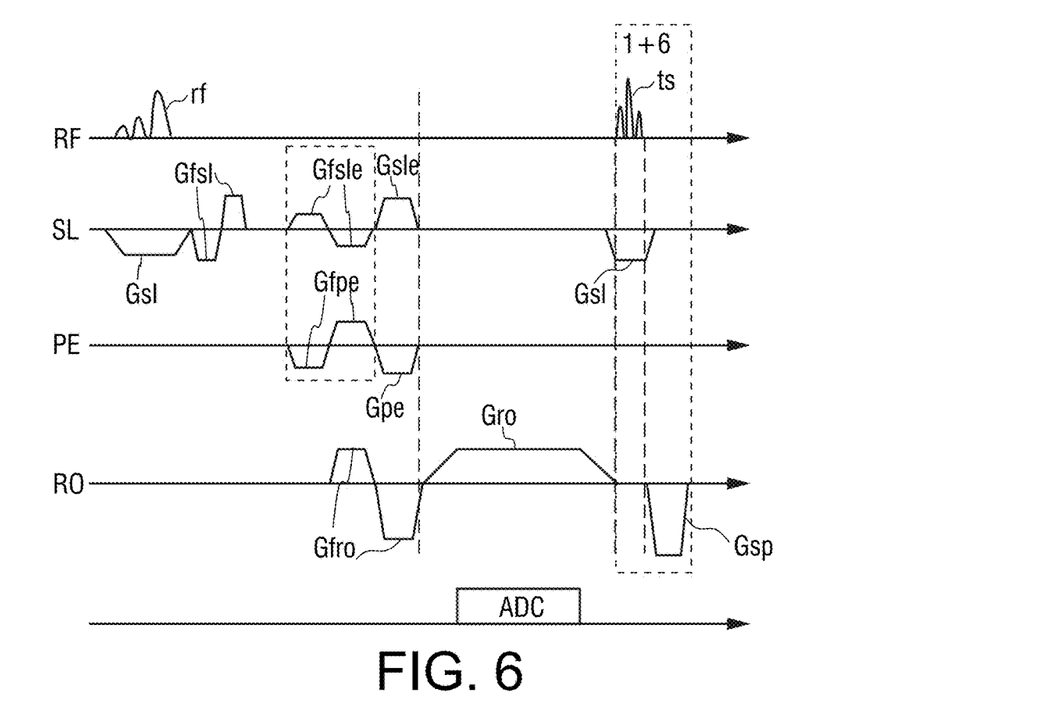
FIG. 6 is a schematic diagram of a TOF sequence according to an exemplary embodiment of the present disclosure.

Further, in FIG. 3, spoiler gradients Gsp of the same length are applied in the Z, Y and X directions of the magnetic field; in FIG. 4, spoiler gradients Gsp of the same length are applied only in the Y and X directions of the magnetic field; in FIG. 5, spoiler gradients Gsp of the same length are applied only in the Z and X directions of the magnetic field; and in FIG. 6, a spoiler gradient is applied only in the X direction of the magnetic field.

Figure 7:
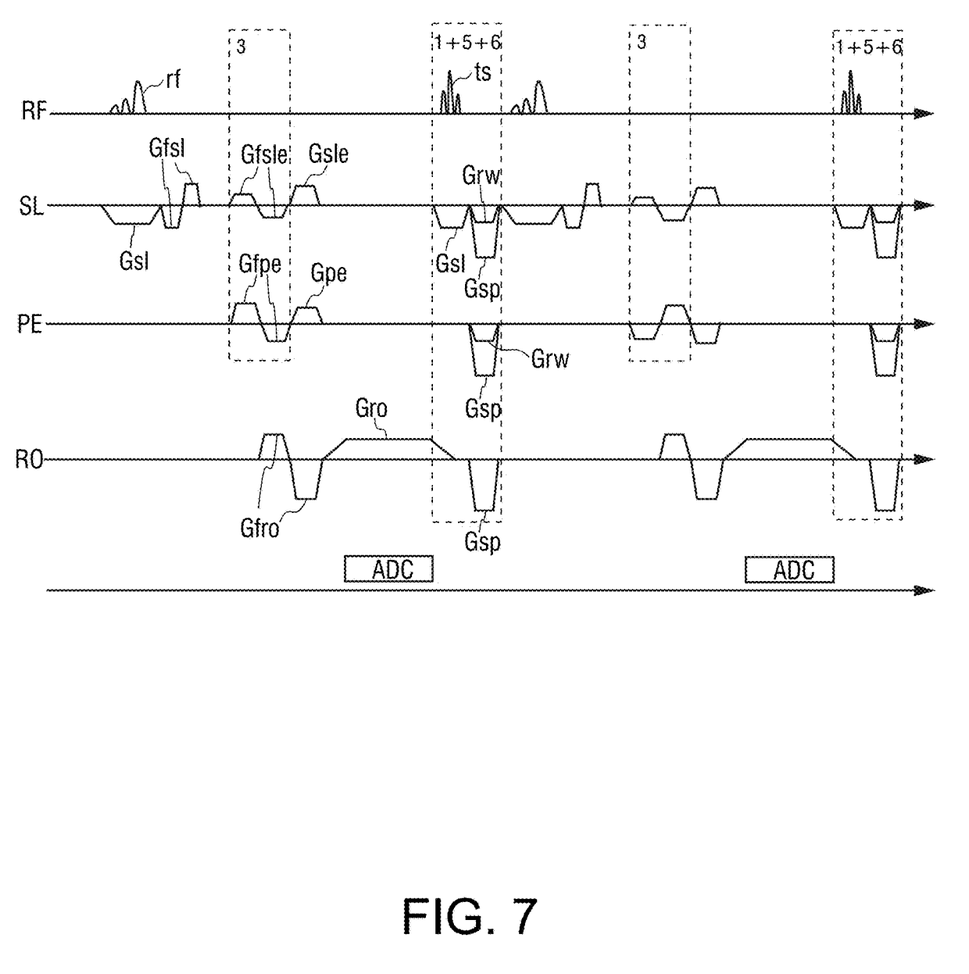
FIG. 7 is a schematic diagram of a TOF sequence according to an exemplary embodiment of the present disclosure.

In the TOF sequence shown in FIG. 7, spoiler gradients Gsp of the same length are applied in the Z, Y and X directions of the magnetic field, and refocusing gradients Grw of the same length as the spoiler gradients Gsp are applied in the Z and Y directions of the magnetic field.

As can be seen, FIGS. 3-6 correspond to merging the spoiler gradients in module 1 and module 6 of the existing TOF sequence. FIG. 7 corresponds to merging the spoiler gradients in module 1 and module 6 of the existing TOF sequence, and at the same time superposing the spoiler gradients with the refocusing gradient in module 5.

Figure 8:
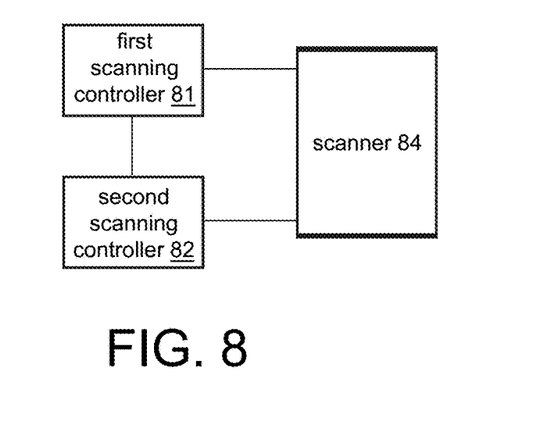
FIG. 8 is a structural schematic diagram of a TOF MRI scanning apparatus according to an exemplary embodiment of the present disclosure.

FIG. 8 is a structural schematic diagram of a TOF MRI scanning apparatus according to an exemplary embodiment of the present disclosure. The apparatus may include a first scanning controller 81 and a second scanning controller 82. In an exemplary embodiment, one or both of the controller 81 and controller 82 includes processing circuitry that is configured to perform one or more respective functions and/or operations of the controllers 81, 82.

In an exemplary embodiment, the first scanning controller 81 is configured to apply a first slice selection gradient in the Z direction of the magnetic field at the same time as applying an RF pulse to the imaging target when a TOF MRI scan begins; apply a slice selection encoding gradient and a phase encoding gradient in the Z direction and Y direction of the magnetic field respectively, after the application of the RF pulse and first slice selection gradient has ended; begin the application of a readout gradient in the X direction of the magnetic field, when the application of the slice selection encoding gradient and phase encoding gradient ends; begin the application of a tracking saturation pulse to the imaging target, and simultaneously begin the application of a second slice selection gradient in the Z direction of the magnetic field, when the application of the readout gradient ends.

The second scanning controller 82 is configured to begin the application of a spoiler gradient in one of the three directions X, Y and Z of the magnetic field or any combination thereof, when the application of the tracking saturation pulse ends.

In an exemplary embodiment, when the application of the tracking saturation pulse ends, the second scanning controller 82 is further configured to: begin the application of a refocusing gradient in one of the two directions Y and Z of the magnetic field or a combination thereof.

In an exemplary embodiment, after applying the first slice selection gradient in the Z direction of the magnetic field, the first scanning controller 81 is further configured to: begin the application of a first flow compensation gradient in the Z direction of the magnetic field, when the application of the first slice selection gradient ends.

In an exemplary embodiment, after the application of the RF pulse and first slice selection gradient has ended, and before applying the slice selection encoding gradient and phase encoding gradient in the Z direction and Y direction of the magnetic field respectively, the first scanning controller 81 is further configured to: apply a second flow compensation gradient and a third flow compensation gradient of the same length in the Z direction and Y direction of the magnetic field simultaneously. In an exemplary embodiment, the application of the slice selection encoding gradient and phase encoding gradient in the Z direction and Y direction of the magnetic field respectively by the first scanning controller 81 comprises: beginning the application of the slice selection encoding gradient and phase encoding gradient in the Z direction and Y direction of the magnetic field respectively when the application of the second flow compensation gradient and third flow compensation gradient ends. In an exemplary embodiment, after beginning the application of the first flow compensation gradient in the Z direction of the magnetic field and before beginning the application of the readout gradient in the X direction of the magnetic field, the first scanning controller 81 is further configured to: apply a fourth flow compensation gradient in the X direction of the magnetic field.

In an exemplary embodiment, the beginning of the application of the readout gradient in the X direction of the magnetic field by the first scanning controller 81 comprises: beginning the application of the readout gradient in the X direction of the magnetic field when the application of flow compensation in the X direction of the magnetic field ends.

The embodiments of the present disclosure further provide an MRI system 83, comprising the TOF MRI scanning apparatus as described above. The MRI system may further include an MR scanner 84 configured to acquire MR image data. The MR scanner 84 may include, for example, magnet unit configured to generate a basic magnetic field, a gradient unit for generating gradient fields, a radiofrequency (RF) transceiver configured to transmit and receive radiofrequency signals, and a patient receiving area for receiving an examination object.

According to the disclosure, the TOF sequence is optimized to form a denser sequence, with certain unnecessary gradients being removed to reduce the TR. This is specifically manifested as follows:

In view of the fact that only gradient momentum can spoil spins with a phase shift exceeding 2π in each voxel, and there is no need to strictly limit which axis the spoiler gradient should be placed on, the spoiler gradients in the existing TOF sequence can be subjected to some deformations, for example: a spoiler gradient is placed on only one axis, or spoiler gradients on three axes are placed together, or spoiler gradients are placed on two axes; in order to achieve this deformation, first of all the tracking saturation pulse is moved to a position after the readout gradient, then the spoiler gradients that immediately follow the tracking saturation pulse and the readout gradient in the existing TOF sequence are merged at a position after the tracking saturation pulse, thereby obtaining the present disclosure.

It must be explained that the placement of the tracking saturation pulse at the end of the TOF sequence will not produce any negative effects, because there are generally always a few false scans before the actual imaging scan begins.

Furthermore, in order to retain the refocusing gradient and reduce alteration of the existing TOF sequence as much as possible, a refocusing pulse can be applied at the same time as the spoiler gradient is applied in the Z direction or/and Y direction of the magnetic field.

Furthermore, according to the Bloch equations:

$$M_{xy} = M_z \sin(\theta) e^{\frac{-TE}{T2}} = \frac{M_0 \sin(\theta)(1 - e^{\frac{-TR}{T1}})}{(1 - e^{\frac{-TR}{T1}} \cos(\theta))} * e^{\frac{-TE}{T2}}$$

where $M_{xy}$ is the transverse component of the magnetization vector M, $M_z$ is the longitudinal component of the magnetization vector M, $M_0$ is the magnetization vector in an equilibrium state, T1 is the longitudinal relaxation time, T2 is the transverse relaxation time, TE is the echo time, TR is the repetition time, and θ is the angle between the magnetization vector M and the Z axis.

Clearly: when TR decreases while other parameters remain unchanged, the signal strength of background tissue will decrease; thus, because TR is reduced in the embodiments of the present disclosure, the contrast between foreground (e.g. arteries) and background tissue will be enhanced.

A real test example of the present disclosure is given below:

An in vivo experiment was performed on a 3T magnetic resonance spectrum system, and an examination of the arteries in a volunteer's head was performed using a 16-channel head-and-neck coil. The protocol parameters were as follows:

FOV (imaging field of view)=200×180, TE (echo time) =3.73 ms (milliseconds), number of slices per excitation=40, slice thickness=0.5 mm (millimeters), BW (bandwidth)/pixel=186 HZ (Hertz), matrix (i.e. image resolution) size=384×331, slice oversampling rate (OS)=20%, voxel size=0.3 mm×0.3 mm×0.5 mm, flip angle=18°, tonal gradient=70%;

wherein, when the existing TOF sequence is used to perform an MRI scan, TR=23 s and the scan time=6 minutes 3 seconds; when the TOF sequence provided in an embodiment of the present disclosure is used to perform an MRI scan, TR=21 ms and the scan time=5 minutes 40 seconds.

Figure 9:
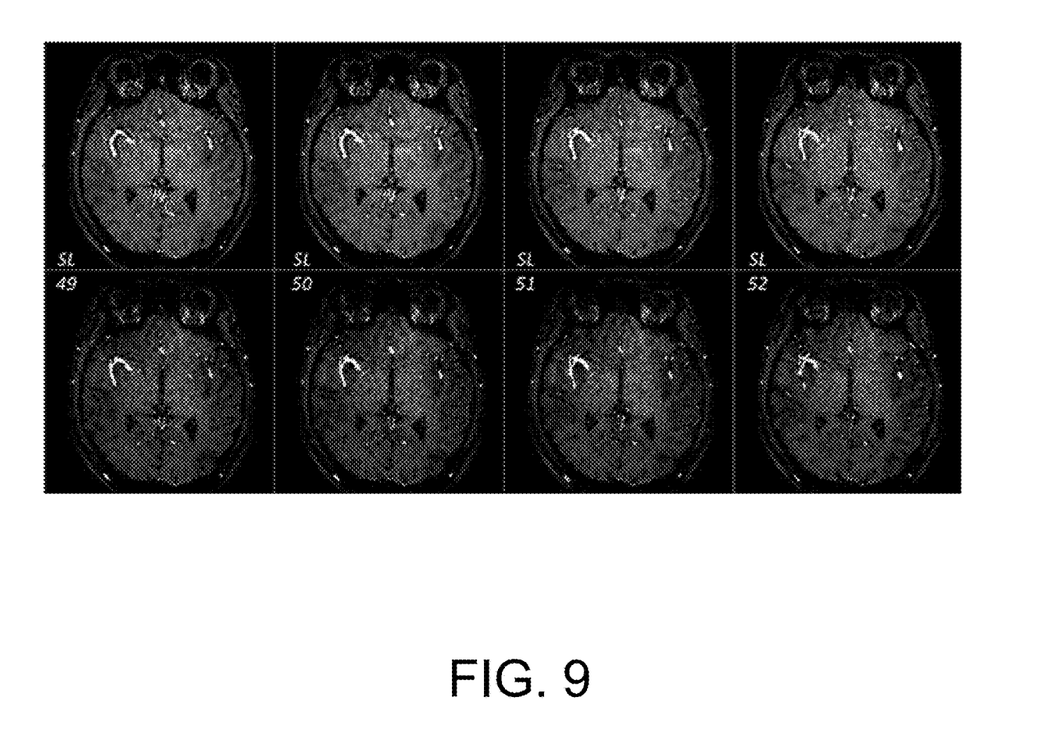
FIG. 9 compares the MRI images of blood vessels obtained by using the existing TOF sequence and the TOF sequence according to an embodiment of the present disclosure for scanning in a test example applying the present disclosure.

FIG. 9 compares the MRI images of blood vessels obtained by using the existing TOF sequence and the TOF sequence provided in an embodiment of the present disclosure for scanning in one example, wherein the upper 4 images were obtained by using the existing TOF sequence for scanning, and the lower 4 images were obtained by using the TOF sequence provided in an embodiment of the present disclosure for scanning. As can be seen, the lower 4 images display a better background suppression effect, and thus increase the contrast between arteries and background tissue.

Figure 10:
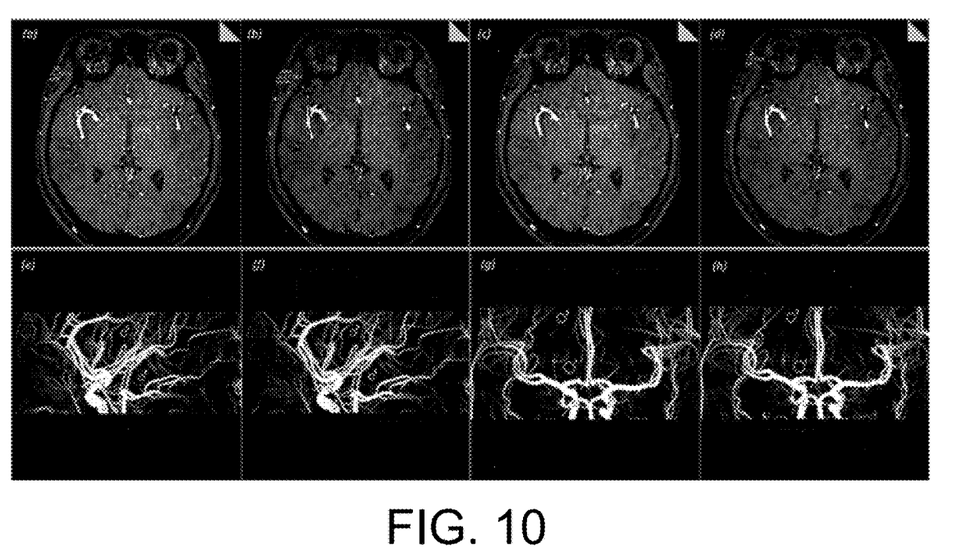
FIG. 10 compares the MRI images of blood vessels obtained by using the existing TOF sequence and the TOF sequence according to an embodiment of the present disclosure for scanning in another test example applying the present disclosure.

FIG. 10 compares the MRI images of blood vessels obtained by using the existing TOF sequence and the TOF sequence provided in an embodiment of the present disclosure for scanning in another example, wherein a, c, e and g are MRI images of blood vessels obtained by using the existing TOF sequence for scanning, and b, d, f and h are MRI images of blood vessels obtained by using the TOF sequence provided in an embodiment of the present disclosure for scanning. By performing quantitative calculation of the mean values and variances of images a-h, it is also found that: the contrast between arteries and background tissue in b, d, f and h is quantitatively increased relative to a, c, e and g.

Figure 11:
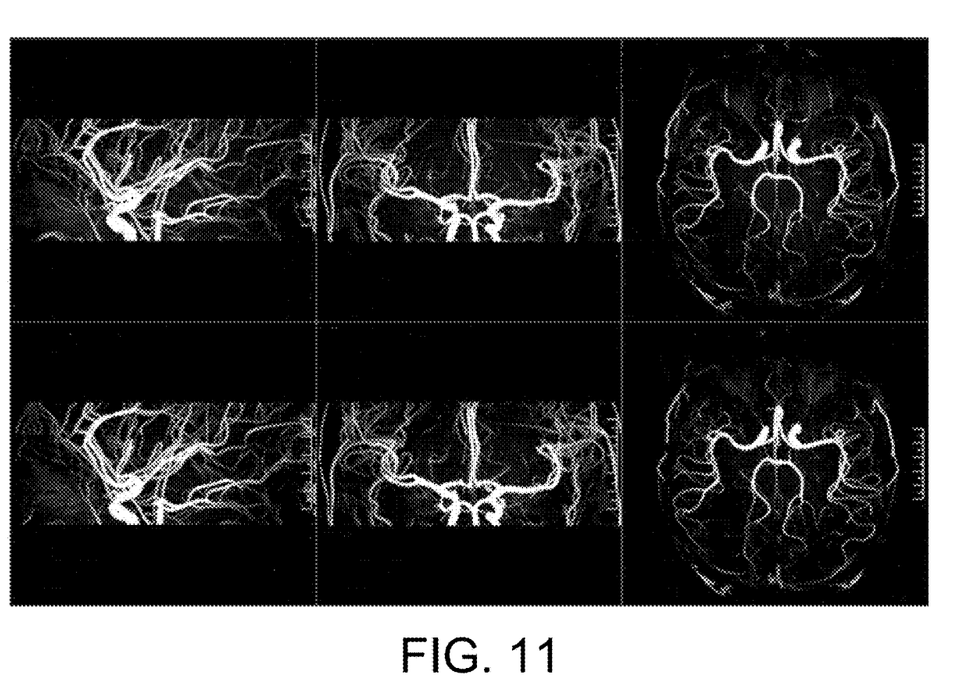
FIG. 11 compares the MRI images of blood vessels obtained by using the existing TOF sequence and the TOF sequence according to an embodiment of the present disclosure for scanning in another test example applying the present disclosure.

FIG. 11 compares the MRI images of blood vessels obtained by using the existing TOF sequence and the TOF sequence provided in an embodiment of the present disclosure for scanning in another example, wherein the upper 3 images were obtained by using the existing TOF sequence for scanning, and the lower 3 images were obtained by using the TOF sequence provided in an embodiment of the present disclosure for scanning. As can be seen, in the lower 3 images, the details of the arteries are clearer, and the contrast between blood vessels and the background is increased.

The example of FIG. 9 above shows that: the dense TOF sequence provided in an embodiment of the present disclosure has a good suppressing effect on the background tissue signal; the example of FIG. 10 shows that: the strength of the blood vessel signal is slightly increased, while the background tissue signal is suppressed, such that the contrast between the blood vessels and the background is somewhat enhanced; and the example of FIG. 11 shows that: blood vessels are displayed in greater detail, and the signal is smoother.

It must be explained that the dense TOF sequence provided in an embodiment of the present disclosure will not have the issue of signal discontinuity that occurs in segmented TOF imaging, and thus can be combined directly with other accelerating techniques such as compression.

The embodiments above are merely preferred embodiments of the present disclosure, which are not intended to limit it. Any amendments, equivalent substitutions or improvements etc. made within the spirit and principles of the present disclosure shall be included in the scope of protection thereof.

To enable those skilled in the art to better understand the solution of the present disclosure, the technical solution in the embodiments of the present disclosure is described clearly and completely below in conjunction with the drawings in the embodiments of the present disclosure. Obviously, the embodiments described are only some, not all, of the embodiments of the present disclosure. All other embodiments obtained by those skilled in the art on the basis of the embodiments in the present disclosure without any creative effort should fall within the scope of protection of the present disclosure.

It should be noted that the terms "first", "second", etc. in the description, claims and abovementioned drawings of the present disclosure are used to distinguish between similar objects, but not necessarily used to describe a specific order or sequence. It should be understood that data used in this way can be interchanged as appropriate so that the embodiments of the present disclosure described here can be implemented in an order other than those shown or described here. In addition, the terms "comprise" and "have" and any variants thereof are intended to cover non-exclusive inclusion. For example, a process, method, system, product or equipment comprising a series of steps or modules or units is not necessarily limited to those steps or modules or units which are clearly listed, but may comprise other steps or modules or units which are not clearly listed or are intrinsic to such processes, methods, products or equipment.

References in the specification to "one embodiment," "an embodiment," "an exemplary embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The exemplary embodiments described herein are provided for illustrative purposes, and are not limiting. Other exemplary embodiments are possible, and modifications may be made to the exemplary embodiments. Therefore, the specification is not meant to limit the disclosure. Rather, the scope of the disclosure is defined only in accordance with the following claims and their equivalents.

Embodiments may be implemented in hardware (e.g., circuits), firmware, software, or any combination thereof. Embodiments may also be implemented as instructions stored on a machine-readable medium, which may be read and executed by one or more processors. A machine-readable medium may include any mechanism for storing or transmitting information in a form readable by a machine (e.g., a computer). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others.

Further, firmware, software, routines, instructions may be described herein as performing certain actions. However, it should be appreciated that such descriptions are merely for convenience and that such actions in fact results from computing devices, processors, controllers, or other devices executing the firmware, software, routines, instructions, etc. Further, any of the implementation variations may be carried out by a general-purpose computer.

For the purposes of this discussion, the term "processing circuitry" shall be understood to be circuit(s) or processor(s), or a combination thereof. A circuit includes an analog circuit, a digital circuit, data processing circuit, other structural electronic hardware, or a combination thereof. A processor includes a microprocessor, a digital signal processor (DSP), central processor (CPU), application-specific instruction set processor (ASIP), graphics and/or image processor, multi-core processor, or other hardware processor. The processor may be "hard-coded" with instructions to perform corresponding function(s) according to aspects described herein. Alternatively, the processor may access an internal and/or external memory to retrieve instructions stored in the memory, which when executed by the processor, perform the corresponding function(s) associated with the processor, and/or one or more functions and/or operations related to the operation of a component having the processor included therein. In one or more of the exemplary embodiments described herein, the memory is any well-known volatile and/or non-volatile memory, including, for example, read-only memory (ROM), random access memory (RAM), flash memory, a magnetic storage media, an optical disc, erasable programmable read only memory (EPROM), and programmable read only memory (PROM). The memory can be non-removable, removable, or a combination of both.

REFERENCE LIST

RF radio frequency sequence
SL slice selection sequence
PE phase encoding sequence
RO readout sequence
Rf radio frequency pulse
Ts tracking saturation pulse
Gsl slice selection gradient
Gfsl flow compensation gradient for slice selection gradient
Gsle slice selection encoding gradient
Gfsle flow compensation gradient for slice selection encoding gradient
Gpe phase encoding gradient
Gfpe flow compensation gradient for phase encoding gradient
Gro readout gradient
Gfro flow compensation gradient for readout gradient
Grw refocusing gradient
Gsp spoiler gradient
201-205 operations
81 first scanning controller
82 second scanning controller

The invention claimed is:
1. A Time-of-flight (TOF) magnetic resonance imaging (MRI) scanning method, comprising:
 initiating a TOF MRI scan that includes applying a first slice selection gradient in a Z direction of a magnetic field and applying, at a same time, a radio frequency (RF) pulse to an imaging target;

in response to the application of the RF pulse and first slice selection gradient having ended, applying a slice selection encoding gradient and a phase encoding gradient in the Z direction and Y direction of the magnetic field, respectively;

in response to the application of the slice selection encoding gradient and phase encoding gradient having ended, initiating application of a readout gradient in an X direction of the magnetic field;

in response to the application of the readout gradient having ended, simultaneously initiating application of a tracking saturation pulse to the imaging target and application of a second slice selection gradient in the Z direction of the magnetic field; and in response to the application of the tracking saturation pulse having ended, initiating application of a spoiler gradient in the X, Y, and/or Z directions of the magnetic field.

2. The method as claimed in claim 1, further comprising: initiating application of a refocusing gradient in the Y and/or Z directions of the magnetic field in response to the application of the tracking saturation pulse having ended.

3. The method as claimed in claim 1, further comprising: in response to the application of the first slice selection gradient in the Z direction of the magnetic field having ended, initiating application of a first flow compensation gradient in the Z direction of the magnetic field.

4. The method as claimed in claim 3, wherein:
in response to the application of the RF pulse and first slice selection gradient having ended, and before the application of the slice selection encoding gradient and phase encoding gradient in the Z direction and Y direction of the magnetic field respectively, the method further comprises: simultaneously applying a second flow compensation gradient and a third flow compensation gradient of a same length in the Z direction and Y direction of the magnetic field, respectively; and the application of the slice selection encoding gradient and phase encoding gradient in the Z direction and Y direction of the magnetic field respectively comprises: initiating the application of the slice selection encoding gradient and phase encoding gradient in the Z direction and Y direction of the magnetic field respectively in response to the application of the second flow compensation gradient and third flow compensation gradient having ended.

5. The method as claimed in claim 3, wherein:
after initiating the application of the first flow compensation gradient in the Z direction of the magnetic field and before initiating the application of the readout gradient in the X direction of the magnetic field, the method further comprises: applying a second flow compensation gradient in the X direction of the magnetic field; and the initiating the application of the readout gradient in the X direction of the magnetic field comprises: initiating the application of the readout gradient in the X direction of the magnetic field in response to the application of the second flow compensation in the X direction of the magnetic field having ended.

6. The method as claimed in claim 1, wherein:
in response to the application of the RF pulse and first slice selection gradient having ended, and before the application of the slice selection encoding gradient and phase encoding gradient in the Z direction and Y direction of the magnetic field respectively, the method further comprises: simultaneously applying a first flow compensation gradient and a second flow compensation gradient of a same length in the Z direction and Y direction of the magnetic field, respectively; and the application of the slice selection encoding gradient and phase encoding gradient in the Z direction and Y direction of the magnetic field respectively comprises: initiating the application of the slice selection encoding gradient and phase encoding gradient in the Z direction and Y direction of the magnetic field respectively in response to the application of the first flow compensation gradient and second flow compensation gradient having ended.

7. A non-transitory computer-readable storage medium with an executable program stored thereon, that when executed, instructs a processor to perform the method of claim 1.

8. A Time-of-flight (TOF) magnetic resonance imaging (MRI) scanning apparatus, comprising:
a first scanning controller configured to:
initiate a TOF MRI scan that includes applying a first slice selection gradient in a Z direction of a magnetic field and applying, at a same time, a radio frequency (RF) pulse to an imaging target;

in response to the application of the RF pulse and first slice selection gradient having ended, apply a slice selection encoding gradient and a phase encoding gradient in the Z direction and Y direction of the magnetic field, respectively;

in response to the application of the slice selection encoding gradient and phase encoding gradient having ended, initiate application of a readout gradient in an X direction of the magnetic field; and in response to the application of the readout gradient has ended, simultaneously initiate: application of a tracking saturation pulse to the imaging target and application of a second slice selection gradient in the Z direction of the magnetic field; and a second scanning controller configured to initiate application of a spoiler gradient in the X, Y and/or Z directions of the magnetic field in response to the application of the tracking saturation pulse having ended.

9. The apparatus as claimed in claim 8, wherein the second scanning controller is further configured to: in response to the application of the tracking saturation pulse having ended, initiate application of a refocusing gradient in the Y and/or Z directions of the magnetic field.

10. The apparatus as claimed in claim 8, wherein the first scanning controller is further configured to: in response to the application of the first slice selection gradient having ended, initiate application of a first flow compensation gradient in the Z direction of the magnetic field.

11. The apparatus as claimed in claim 10, wherein:
the first scanning controller is further configured to: simultaneously apply a second flow compensation gradient and a third flow compensation gradient of a same length in the Z direction and Y direction of the magnetic field, respectively, in response to the application of the RF pulse and first slice selection gradient having ended and before the application of the slice selection encoding gradient and phase encoding gradient in the Z direction and Y direction of the magnetic field, respectively;

the initiation of the application of the slice selection encoding gradient and phase encoding gradient in the Z direction and Y direction of the magnetic field, respectively, by the first scanning controller is in response to the application of the second flow compensation gradient and third flow compensation gradient having ended;

the first scanning controller is further configured to apply a fourth flow compensation gradient in the X direction of the magnetic field in response to the initiation of the application of the first flow compensation gradient in the Z direction of the magnetic field having ended and before initiation of the application of the readout gradient in the X direction of the magnetic field; and the initiation of the application of the readout gradient in the X direction of the magnetic field by the first scanning controller is in response to the application of the fourth flow compensation in the X direction of the magnetic field having ended.

12. The apparatus as claimed in claim 8, wherein:

the first scanning controller is further configured to:
simultaneously apply a first flow compensation gradient and a second flow compensation gradient of a same length in the Z direction and Y direction of the magnetic field, respectively, in response to the application of the RF pulse and first slice selection gradient having ended and before the application of the slice selection encoding gradient and phase encoding gradient in the Z direction and Y direction of the magnetic field, respectively;

the initiation of the application of the slice selection encoding gradient and phase encoding gradient in the Z direction and Y direction of the magnetic field, respectively, by the first scanning controller is in response to the application of the first flow compensation gradient and second flow compensation gradient having ended;

the first scanning controller is further configured to apply a third flow compensation gradient in the X direction of the magnetic field before initiation of the application of the readout gradient in the X direction of the magnetic field; and the initiation of the application of the readout gradient in the X direction of the magnetic field by the first scanning controller is in response to the application of the third flow compensation in the X direction of the magnetic field having ended.

13. A magnetic resonance imaging (MRI) system, comprising:

a Time-of-flight (TOF) magnetic resonance imaging (MRI) scanning apparatus, comprising:
a first scanning controller configured to:
initiate a TOF MRI scan that includes applying a first slice selection gradient in a Z direction of a magnetic field and applying, at a same time, a radio frequency (RF) pulse to an imaging target;
in response to the application of the RF pulse and first slice selection gradient having ended, apply a slice selection encoding gradient and a phase encoding gradient in the Z direction and Y direction of the magnetic field, respectively;
in response to the application of the slice selection encoding gradient and phase encoding gradient having ended, initiate application of a readout gradient in an X direction of the magnetic field; and
in response to the application of the readout gradient has ended, simultaneously initiate: application of a tracking saturation pulse to the imaging target and application of a second slice selection gradient in the Z direction of the magnetic field; and a second scanning controller configured to initiate application of a spoiler gradient in the X, Y and/or Z directions of the magnetic field in response to the application of the tracking saturation pulse having ended.

14. The MRI system as claimed in claim 13, further comprising a magnetic resonance scanner that is communicatively coupled to the TOF MRI scanning apparatus.

* * * * *